US005161526A

United States Patent [19]

[11] Patent Number: 5,161,526

Hellwing et al.

[45] Date of Patent: Nov. 10, 1992

[54] METHOD OF TREATING OF BLEEDING IN HEMOPHILIACS

[76] Inventors: Isak A. Hellwing; Malca Lerman, both of 13 Yam Hamelach Street, Ganei Tikvah 55900, Israel

[21] Appl. No.: 671,130

[22] Filed: Mar. 18, 1991

Related U.S. Application Data

[63] Continuation-in-part of Ser. No. 332,896, Apr. 4, 1989, abandoned.

[51] Int. Cl.[5] ........................ A61N 5/06

[52] U.S. Cl. ........................ 128/395; 128/898; 606/3

[58] Field of Search ........................ 128/395, 397, 382, 898; 606/2, 3, 9, 13–19

[56] References Cited

U.S. PATENT DOCUMENTS

| | | | |
|---|---|---|---|
| 3,642,007 | 2/1972 | Roberts et al. | 606/3 |
| 4,564,011 | 1/1986 | Goldman | 606/9 |
| 4,931,053 | 6/1990 | L'Esperance, Jr. | 128/395 |

*Primary Examiner*—David M. Shay
*Attorney, Agent, or Firm*—Leonard Bloom

[57] ABSTRACT

A method of treating hemophiliac patients suffering injuries due to internal bleeding in the areas of muscles and joints, said bleeding resulting in hematoma or hemarthrosis with concomitant pain and swelling, by biostimulation of the affected area of said muscle and joint, with at least one beam of light with wavelength in the range of 500–1100 nanometers for at least three minutes with an intensity sufficient to reduce the said hematoma or hemarthrosis.

14 Claims, No Drawings

METHOD OF TREATING OF BLEEDING IN HEMOPHILIACS

CROSS REFERENCE TO RELATED APPLICATION

The present application is a continuation-in-part of application Ser. No. 332,896 filed Apr. 4, 1989 now abandoned and the disclosure of which is incorporated herein in its entirety.

FIELD OF THE INVENTION

The present invention relates to a method for treatment of bleeding injuries in hemophiliac patients.

BACKGROUND OF THE INVENTION

Hemophilia is an inherited bleeding disorder caused by a missing clotting factor (Factor 8 in hemophilia A, and Factor 9 in hemophilia B). Hemophiliac patients suffer from bleeding mainly to the joints and muscles, which can be caused by even minor injuries. The bleeding, which can occur as often as two to three times per week, swells the affected area and causes enormous pain and limitation of joint movement and if not stopped can lead to death. Repeated bleeding attacks, if inadequately treated, gradually destroy the joints and can cause permanent handicaps.

The conventional treatment for injured hemophiliacs is the administration of infusions of the missing clotting factor. If there is no improvement within 12 hours of the first infusion, repeated infusions are given at 12 hour intervals until the joint recovers or the muscle hematoma subsides.

Infusions of clotting factors are very expensive. First of all these are administered in hospitals or special medical facilites and they run in the order of about up to $500 per infusion. About 10-15% of the patients develop antibodies against the clotting factor. Such patients require infusions of a special drug, which is even more expensive than the factor himself. For one such bleeding occurrence, an average patient requires a number of infusions, which can add up to a cost of about $5,000 or more. In addition, the infusions, which are manufactured from blood units, cause many complications ranging from transmission of viral diseases (hepatitis and even AIDS) to damage of the immune system.

Moreover, for the first several hours after infusion, the joint range of motion remains limited. Only after about 24 hours is the joint motion better than at the start of the bleeding, but it is still far from the baseline movement before the bleeding. Physical therapy, such as transcutaneous nerve electric stimulation, can enhance the recovery significantly.

The use of light in healing is not new. Even Hypocrates (460-370 B.C.) treated the ill on beds situated inside caves that had some light focused on them through openings in the ceilings. Hendride Mondeville (1120-1320 C.E.) in France used sunlight through red window coverings to treat scarring from smallpox with great success. In modern times, biostimulation with light waves has also become prominent, particularly the use of low-power ("cold" or "soft") lasers, i.e. having energies below 100 milliwatts, have been recognised as a prominent mode of therapy for the treatment of pain, inflammatory conditions, neurogenic disorders and in healing wounds, burns, ulcers, tendons and bones. A review on this subject entitled "Laser Biostimulation of Healing Wounds: Specific Effects and Mechanism of Action" by Chukuka S. Enwemeka, was published in the Journal of Orthopaedic and Sports Physical Therapy—April 1988, pages 33-338.This technique of biostimulation with light energy, specifically low-power lasers, has been used so far exclusively for the treatment of normal people having the usual blood clotting factors and who were never in danger of profuse bleeding which can lead to death.

Lasers of higher energy were also used for surgical purposes and are known as surgical lasers in the medical field. Such lasers are used to cut, burn or fuse tissues, but not in a therapeutic manner. One such laser device is disclosed by L. Goldmann in U.S. Pat. No. 4,564,001, wherein the laser optic probe device is used by penetrating the skin and entering a blood vessel or the tissue immediately adjacent a damaged blood vessel for creating white scar tissue, causing the vessel to shrink in size and at least partially disappear from view. This method produces heat-induced blood clots at the point where the probe enters the vessel. The lasers used by Goldmann have an energy of 2 to 5 watts. Goldmann also discloses that this method could be used if required in emergency clotting of blood such as in the case of hemophilia. But, as stated above, this method requires penetrating the skin to enter the blood vessel and in effect fusing or scarring the vessel to block any flow of blood. This, of course, requires that each single point of damage is treated separately.

SUMMARY OF THE INVENTION

It is thus the object of the present invention to provide a rapid and effective method of enhancing the healing of joints and muscles of bleeding hemophiliacs in a non-invasive and less expensive manner than by conventional methods of treatment.

It is a further object of the present invention to provide a method for treatment of injuries in hemophiliacs which does not require expensive medical facilities, but can be administered by the patient himself at home.

In accordance with this invention there is thus provided a method of treating hemophiliac patients suffering injuries due to internal bleeding in the areas of muscles and joints, said bleeding resulting in hematoma or hemarthrosis with concomitant pain and swelling, by biostimulation of the affected area of said muscle and joint, with at least one beam of light with wavelength in the range of 500-1100 nanometers for at least three minutes with an intensity sufficient to reduce the said hematoma or hemarthrosis.

In a preferred method, the light beam is a low energy laser with a power of under 100 miliwatts and preferably between 1-7 milliwatts.

According to another preferred embodiment, the treatment area is irradiated by at least one traverse of the area by the light beam. Alternatively, the treatment may be by local irradiation in one spot.

Yet another preferred embodiment includes the irradiation with a plurality of light beams.

Irradiation may continue between three minutes and one half hour at a frequency from twice a day to every other day, depending on the type of injury, the type of light used and the reaction of the specific patient to the treatment.

DETAILED DESCRIPTION OF THE INVENTION

As stated earlier, a soft laser is a low energy laser with power below 100 milliwatts. Examples of such lasers are helium-neon lasers, infra-red lasers or a combination of infra-red and helium-neon lasers, to mention a few. The laser may operate either as an impulse or a continuous beam laser. Examples of suitable lasers for use in the method are those marketed by Medical Electronics GmbH, Germany, and Medec AG, Switzerland, for biostimulating devices.

In general the soft laser treatment of hemophiliacs is operative to accelerate healing of hematomas, hemarthrosis, crythema, synovitis, open wounds, inflammations, and similar problems, as well as reducing the concomitant pain. The laser treatment is generally given after one infusion of blood concentrate, which is supposed to stop the bleeding. The soft laser treatment then enhances the recovery of the joint or muscle. In some cases, laser treatment alone is effective.

Preliminary results indicate that the soft laser treatment can enhance recovery of joints and muscles even better, and in shorter time, than physical therapy. The treatment with the soft laser is without known complications, simple to use and can be used at home by the patient.

The intensity, duration and frequency of the irradiation treatment depend on a number of factors: the location of the injury, its size and depth, the amount of time which has elapsed between the occurrence of the injury and the treatment, and which laser is used and which mode of operation.

The treated area may be irradiated by local irradiation in one spot or by one or more traverses of the treated area by the laser beam. Any number of laser diodes may be employed, thus permitting simultaneous irradiation by a plurality of beams, particularly when a large area is to be treated.

Irradiation may continue between 3 minutes and one half hour, from twice a day to every other day, depending upon the type of laser and its mode of operation. For example irradiation with a helium-neon laser, used for more superficial wounds, is generally about three times as long as that with an infra-red laser, which is preferred for deeper wounds.

Test results of a pilot study conducted by a team at the Israel National Hemophilia Center at Tel-Hashomer Hospital are listed, by way of example only, in Table I. All treatments were carried out with an infra-red continuous laser, model LSI 2030, FLA09 of Medical Electronics GmbH. The study suggests enhanced absorption of the bleeding by the soft laser treatment, reduction of pain and, in many cases, reduction in the required number of infusions with their related complications and cost.

It is a particular feature of the present invention that the normal process of healing and absorption of blood is enhanced or accelerated. It is unclear whether the laser treatment stops the bleeding, but it provides a significant improvement in joint movement and reduction of pain. It serves to prevent further damage to the joint or muscle by accelerating the absorption of the blood therefrom. Thus, there appears to be less need for second or additional infusions, with attendant cost savings.

The scientific knowledge relevant to soft laser healing suggests that biostimulation with a soft laser (1) accelerates the inflammatory phase of wound healing by altering the levels of various prostaglandins, (2) increases APT synthesis by enhancing electron transfer in the inner membrane of mitochondria, (3) quickens protein (collagen) synthesis by quickening DNA and RNA synthesis, (4) augments fibroplasia by a mechanism that is still being explored, and (5) enhances the ability of immune cells to combat invading pathogens.

When using light sources other than lasers for biostimulation in treating hemophiliac bleeding in accordance with the invention, we have found the instruments of Medical Electronics GmbH to be quite satisfactory. These instruments have multiple light sources disposed in a manner to fit the anatomy of the body parts requiring treatment. For example, their Hyper-Photon 3D Photostimulation instrument comprises 128 high performance LEDs.

It will be appreciated by those skilled in the art that the invention is not limited to what has been shown and described hereinabove by way of example. Rather, the scope of the invention is limited solely by the claims which follow.

TABLE I

| PATIENT NUMBER | DESCRIPTION OF INJURY | RESULTS OF FIRST TREATMENT | RESULTS OF 2ND TREATMENT |
|---|---|---|---|
| 1 | Bleeding in shin. Hematoma and swelling 26.5 × 27.5 cm Great pain. | $\frac{1}{2}$ hour laser treatment. Reduction of swelling and hematoma to 26 × 27 cm. No infusion required. Pain ceased. | No second treatment needed. |
| 2 | Bleeding in the muscles of the left knee. Difficulty in movement. Swelling and hematoma 30 × 31.5 cm. Medium to strong pain. | $\frac{1}{4}$ hour laser treatment. No change in size (still 30 × 31.5) but improvement in movement. No pain. | No second treatment needed. No infusion needed |
| 3 | Hematoma in the right elbow of 20 cm. | 15 minutes laser treatment Reduction to 29.4 cm. | Repeat laser treatment one hour later lasting 15 minutes. Hematoma reduced to 19 cm. No infusion needed. |
| 4 | Bleeding in the right elbow. Straightening elbow limited to 50°, bending limited to 80°. | 3 minutes laser treatment. 5° improvement in bending and straightening elbow. | 5 minutes laser treatment immediately after the first treatment. Improvement of another 5° in bending and straightening the elbow. |
| 5 | Bleeding in right knee. Hematoma with swelling 31.5 × 31.9 cm. Great pain. | 3 minutes laser treatment. Reduction of swelling and hematoma to 31.3 × 31.2. Medium pain. Difficulty in straightening the knee. | 3 minutes laser treatment one hour after first treatment Hematoma reduced to 31 × 31.2. Pain disappeared. No infusion needed. Substantial improvement in straightening. |
| 6 | Bleeding in left shin. | 3 minutes laser treatment. No | 8 minutes laser treatment |

TABLE I-continued

| PATIENT NUMBER | DESCRIPTION OF INJURY | RESULTS OF FIRST TREATMENT | RESULTS OF 2ND TREATMENT |
|---|---|---|---|
| | Hematoma and swelling 1.6 cm. | difference. | after first treatment. Reduction of hematoma and swelling of 8 mm. |
| | Bleeding in right shoulder. Great pain. Hematoma of about 30 cm. | 8 minutes laser treatment. No difference. | 8 minutes laser treatment after first treatment. Pain ceased and hematoma shrank by 2 mm. |
| 8 | Bleeding in left ankle. Hematoma of 10 × 27 cm without pain. | 3 minutes laser treatment. Hematoma shrank to 26.5 × 10. | 3 minutes laser treatment one hour after first treatment. Reduction of swelling to 26.0 × 10 cm. |
| 9 | Bleeding in left shoulder with sharp pain. | 3 minutes laser treatment. Bleeding and pain ceased. | |
| 10 | Bleeding in left sole. Hard, swollen hematoma of 31.4 cm of dark color. | 3 minutes laser treatment. Hematoma did not shrink but the color became much lighter and the hematoma became softer. | Received no infusion or second treatment. After two days, the hematoma disappeared. |
| 11 | Hemarthrosis in the right knee 27.6 cm. Hemarthrosis in the left knee 24.2 cm. | 15 minutes laser treatment Hemarthrosis reduced in right knee to 26 cm and in left knee to 23 cm. | 4 minutes laser treatment. Hemarthrosis in right knee reduced to 25 cm. and in left knee to 20 cm. Received no infusion at all |
| 12 | Large, hard hematoma around the ankle hematoma preventing movement. | 30 minutes laser treatment. The hematoma disappeared. Complete freedom of movement. | No second treatment needed. |
| 13 | Hematoma in sciatic nerve Very great pain. | 10 minutes laser treatment Clear clinical improvement immediately after irradiation. | No second treatment needed. |
| 14 | Huge hematoma in right thigh, to the extent of 3.5 cm. Difficulty in bending causing a limp. | 5 minutes laser treatment. Circumference of hematoma shrank to 2.55 cm. Easing of movement. Received no infusion. | 5 minutes laser treatment one hour after first treatment Hematome shrank an additional 1 cm. Free movement permitting riding a bicycle the following day. |
| 15 | Hematoma in left thigh of 26.7 cm. | 15 minutes laser treatment hematoma. reduced to 26 cm. | No second treatment. Received no infusion. |
| 16 | Hematoma in right elbow of 27.6 cm. | 3 minutes laser treatment. Hematoma shrank to 27 cm. Received only one infusion. | Received no second infusion. |
| 17 | Hemarthrosis in right knee of 27 cm. | 15 minutes laser treatment. Size reduced to 24.7 cm. Received one infusion. | No second infusion required. No additional treatment required. |
| 18 | Hematoma in the chest of 7 × 4.5 cm. | 30 minutes laser treatmemt Reduction of hematoma to 3.5 × 6. | No second infusion or treatment required. |

We claim:

1. A method of treating hemophiliac patients suffering injuries due to internal bleeding in affected areas of muscles and joints, said bleeding resulting in hematoma or hemarthrosis with concomitant pain and swelling, including the step of biostimulating the affected area of said muscle and joint, with at least one beam of light with wavelength in a range of 500–1100 nanometers for at least three minutes with an intensity sufficient to reduce said hematoma or hemarthrosis.

2. A method according to claim 1 and wherein the step of biostimulating comprises irradiating the affected area with a plurality of beams.

3. A method according to claim 1 and wherein the step of biostimulating comprises irradiating the affected area with local irradiation in one spot.

4. A method according to claim 1 and wherein the step of biostimulating comprises irradiating the affected area by at least one traverse of the treated area by the light beam or beams.

5. A method according to claim 1 and wherein the step of biostimulating comprises irradiating the affected area between 3 minutes and one half hour in each treatment.

6. A method of treating hemophiliac patients suffering injuries due to internal bleeding in an affected area of muscles and joints, said bleeding resulting in hematoma or hemarthrosis with concomitant pain and swelling, comprising the steps of providing a low energy laser with power below 100 milliwatts and having at least one beam and irradiating the area of said muscle and joint with the at least one beam of said low energy laser for at least three minutes with an intensity sufficient to reduce said hematoma or hemarthrosis.

7. A method according to claim 6 and wherein said step of irradiating comprises irradiating the affected area with a helium-neon laser.

8. A method according to claim 6 and wherein said step of irradiating comprises irradiating the affected area with an infra-red laser.

9. A method according to claim 6 and wherein said step of irradiating comprises irradiating the affected area with a combination helium-neon and infra-red laser.

10. A method according to claim 6 and wherein the step of irradiating comprises irradiating the affected area with local irradiation in one spot.

11. A method according to claim 6 and wherein the step of irradiating comprises irradiating the affected area by at least one traverse of the treated area by the laser beam or beams.

12. A method according to claim 6 and wherein said step of irradiating comprises irradiating the affected area with an helium-neon laser.

13. A method according to claim 6 and wherein said step of irradiating comprises irradiating the affected area with an infra-red laser.

14. A method according to claim 6 and wherein said step of irradiating comprises irradiating the affected area with a combination helium-neon and infra-red laser.

* * * * *